United States Patent [19]
Thomas

[11] Patent Number: 5,811,446
[45] Date of Patent: Sep. 22, 1998

[54] PROPHYLACTIC AND THERAPEUTIC METHODS FOR OCULAR DEGENERATIVE DISEASES AND INFLAMMATIONS AND HISTIDINE COMPOSITIONS THEREFOR

[75] Inventor: Peter G. Thomas, Charlottesville, Va.

[73] Assignee: Cytos Pharmaceuticals LLC, Durham, N.C.

[21] Appl. No.: 839,805

[22] Filed: Apr. 18, 1997

[51] Int. Cl.⁶ .......................... A01N 43/50; C07D 233/60
[52] U.S. Cl. .......................... 514/399; 514/844; 514/912; 514/914; 548/339.1
[58] Field of Search ................................. 514/399, 912, 514/914, 844; 548/339.1

[56] References Cited

PUBLICATIONS

Babizhayev, Biochimica et Biophysica Acta vol. 1004, "Antioxidant activity of L–carnosine, a natural histidine––containing dipeptide in crystalline lens", pp. 363–371, (1989).

Babizhayev, Chemical Abstract vol. 111 No. 167340, "Antioxidant activity of L–carnosne, a natural histidine" (1989).

Santen et al, Chemical abstract vol. 98 No. 149604, "Eye lotions containing an antinflammatory ketopropen" (1983).

*Primary Examiner*—John Kight
*Assistant Examiner*—Raymond Covington
*Attorney, Agent, or Firm*—Isaac A. Angres; Susan P. Petraglia

[57] ABSTRACT

The present invention relates to methods for protecting the eye from degenerative eye conditions by administering prophylactic histidine compositions. The invention also relates to methods for treating ocular inflammation resulting from various causative agents, by administering therapeutic histidine compositions. The invention relates further still to novel histidine compositions for carrying out the present methods.

45 Claims, No Drawings

PROPHYLACTIC AND THERAPEUTIC METHODS FOR OCULAR DEGENERATIVE DISEASES AND INFLAMMATIONS AND HISTIDINE COMPOSITIONS THEREFOR

FIELD OF THE INVENTION

The present invention relates to methods for protecting the eye from degenerative eye conditions by administering prophylactic histidine compositions. The invention also relates to methods for treating ocular inflammation resulting from various causative agents, by administering therapeutic histidine compositions. The invention relates further still to novel histidine compositions for carrying out the present methods.

BACKGROUND OF THE INVENTION

The eye, like other parts of the central nervous system, has limited regeneration capability. Thus, many ocular diseases and injuries are difficult to treat. Presently, there are no truly effective treatments for, for example, retinal photic injury, retinal ischemia-induced eye injury, age-related macular degeneration, and free-radical-mediated diseases and/or injuries. Certain of these degenerations and injuries result in the irreversible destruction of the photoreceptor cells; therefore prophylaxis is the only viable option for management. Loss of vision also arises as a result of ischemia-reperfusion injury that is associated with retinal arterial occlusion, retinal venous occlusion, and glaucoma.

Many ocular degenerations are secondary to other primary compromising conditions, for example, diabetic retinopathy and lupus retinopathy. Corneal degenerations, for example, are usually not inherited, but occur in mid-life or later with lesions that are secondary to primary manifestations of aging, inflammation, trauma, and systemic disease.

The eye is also particularly vulnerable to infection caused by virulent bacteria. The most frequently encountered bacterial infections are believed to be bacterial keratitis, bacterial conjunctivitis, and bacterial blepharitis. The most significant ocular viral infections are caused by the family of herpesviruses (HSV-1, HSV-2, varicella-zoster virus, cytomegalovirus, and Epstein-Barr virus.) Some ocular tissues (e.g., cornea, lens, and vitreous) are avascular with few mesenchymal cells and therefore are highly susceptible to infection. Ocular tissue already compromised due to degenerative injury (e.g., lesions) or physical trauma (e.g., laceration) affords easy entrance to bacteria and viruses. For example, infection can follow superficial or penetrating corneal injury, and the type of offending matter and the time between trauma and therapy are oftentimes determinative of the type and extent of infection. Fungal infection can be seen in surface injuries involving vegetable matter. Another competing consideration is the fact that certain therapeutic agents used to treat ocular injury and/or infection also suppress the host's immunologic defense mechanism, thus rendering the eye susceptible to other types of infections.

Ocular inflammation is a nonspecific result of tissue damage. While there are several agents that can elicit an inflammatory response, microbial (bacterial, viral, or fungal) infection and various immunologic conditions (e.g., hypersensitivity, allergy, and autoimmunity) are the most common causes of ocular inflammation. Inflammation associated with chemical and thermal injury can have a highly destructive outcome on the eye, and especially the cornea. Physical trauma to the cornea may be accompanied by intraocular inflammation, synechiae leading to glaucoma, and secondary membrane formation. Collagen is the major structural protein of the cornea. The normal host response to inflammation produces polymorphonuclear (PMN) leukocytes or corneal fibroblasts which release matrix-destroying enzymes (e.g., collagenases), leading to the destruction of collagen. Also, normal corneal epithelium contains no latent or active collagenases. However, following chemical injury to the eye, these cells have been known to produce the destructive enzyme. Other macromolecules such as proteoglycans and other glycoproteins are also destroyed. Neovascularization is a sequela to the majority of ocular inflammatory responses. Chronic ocular inflammations such as trachoma and inflammation resulting from penetrating corneal injuries lead to scarring of the cornea. This is attributable to the enhanced production of collagen by corneal and conjunctival tissue fibroblasts as potentiated by the presence of inflammatory cells. Stromal scarring (e.g., from stromal edema) disturbs the ordering and spacing of collagen fibrils that are necessary to prevent light scattering, and causes a loss of stromal transparency.

The inflammatory response is a dominant aspect of corneal ulceration (ulcerative keratitis), which is a frequent cause of vision loss. Corneal ulceration has several causes, chiefly viral (e.g., *Herpes simplex* is the most common and is the leading cause of corneal blindness in the U.S.) or bacterial infection (Pseudomonas sp.), chemical (e.g., alkali burn) and thermal injury, and vitamin A and protein deficiencies. Enzymatic breakdown of collagen is the major degenerative aspect of the ulceration. The outcome of ulceration, if untreated, is one or more of perforation of the cornea, formation of opaque scar tissue, and vascular invasion, with ultimate blindness. The inflammatory response is also at work in the corneal stroma in nonulcerative keratitis (also, interstitial keratitis), which has either bacterial, viral, or parasitic origin. Although less frequent than ulcerative bacterial keratitis, interstitial keratitis is a significant cause of visual impairment in developing countries, and the major causes of which are *T. pallidum* (the syphilis bacteria) and *Borrelia burgdorferi* (Lyme disease.)

Refractive surgical procedures aimed at altering corneal curvature for treating myopia and astigmatism, for example, result in a disruption of several corneal components, such as epithelial cells and their adhesion structures, the Bowman's layer and the anterior stroma. Incisional procedures (e.g., radial keratotomy (RK)) utilizing cutting implements invariably damage many layers of cells adjacent to the incision, and hence impair the wound-healing ability without attendant scar formation. The use of UV and non-UV emitting lasers in ocular surgery (e.g., excimer laser keratectomy, photorefractive keratectomy (PRK) and laser in-situ keratomileusis (LASIK)) has evolved to minimize the extent of cell disruption during excisional procedures and to enhance the wound-healing ability of the surgical site. However, despite the improvements of lasers over cutting implements, one of the main drawbacks of corrective laser procedures is the development of "corneal haze", or clouding, leading to light scattering. While many reasons have been postulated as to why the haze develops, the chief theory is that the haze is a scar resulting from improper wound healing. Improper collagen repair and/or alignment, inflammation, and improper epithelial cell coverage of the cornea are believed to play a role in the scar formation. Another drawback of laser procedures is that they set into motion a cascade of free-radical mediated cellular injuries, such as DNA damage, enzyme inactivation, and lipid peroxidation, leading to corneal toxicity which may impact on wound healing and the development of post-operative corneal haze.

Numerous therapies and therapeutic agents have been developed over the years to treat sequelae of ocular degeneration, physical and chemical traumatic ocular injury, and ocular inflammation. While many of these have proven to be useful and provide an acceptable level of therapy and reparation to the damaged eye tissue, others have unacceptable side effects that dispose the already impaired/injured eye to further vulnerability (e.g., toxicity.) For example, corticosteroids have been used topically to reduce corneal scarring and inflammation. However their use is deemed controversial because they are known to enhance bacterial growth or recurrence of ulcers. Many antibiotics (e.g., beta-lactams and certain fluoroquinolones) are not well-tolerated, give rise to toxicities, or are of moderate efficacy. The use of immunosuppressive agents in treating autoimmune ocular disease, e.g., uveitis, is controversial because of many serious side effects including bone marrow depression, thrombocytopenia, bleeding, nausea, vomiting, and stomatitis occur. Without attempting a comprehensive and exhaustive list of agents that have proven beneficial in the management of primary and secondary sequelae of ocular degeneration, injury, surgical trauma, and attendant inflammation, representative classes of compounds include antibacterials(e.g., broad spectrum antibiotics), antivirals, non-steroidal antiinflammatory agents, aminosteroids, collagenase inhibitors, cholinergics, cycloplegics, and wound healing modulators.

The present invention is based upon the surprising discovery, unknown to the relevant art, that the amino acid histidine can be used prophylactically and therapeutically as an active agent in prevention and treatment of ocular degenerative conditions and ocular inflammation, respectively, without the drawbacks of side effects known to existing or abandoned prophylaxes and therapies. Further appreciated by the invention is that therapeutic amounts of histidine are useful in preventing or reducing the incidence of sequelae associated with post-laser surgical wound healing.

OBJECTS OF THE INVENTION

The invention relates to a method of prophylaxis for degenerative eye conditions in a mammal by administering a prophylactically effective amount of histidine to a mammal susceptible to a degenerative eye condition.

The invention relates further to a method for treating ocular inflammation in a mammal associated with one or more of a degenerative eye condition, an infectious agent, an ophthalmic procedure, and an unintentional physical or chemical eye trauma by administering to said mammal a therapeutically effective amount of histidine to reduce ocular inflammation.

The invention relates further still to a method for reducing the sequelae of post-surgical ocular wound healing in a patient, and particularly, post-excimer laser surgery wound healing, by administering to the patient an amount of histidine effective to maintain planar keratocyte regeneration.

The invention also embodies various active histidine compositions intended for administration by various routes to carry out the above methods. Compositions of active histidine in combination with other therapeutic ocular agents are also within the purview of the invention. These and other objects of the invention will make themselves apparent from the following detailed description, non-limiting examples, and from the appended claims.

SUMMARY OF THE INVENTION

The ophthalmological methods according to the invention, and the histidine compostions therefor, are intended for the prophylaxis or treatment of various ocular conditions that lead to at least one or more of the following: cell damage, permanent ocular degeneration, and visual impairment or loss in mammals. While the present methods are intended for application to any mammal wherein interventional ocular therapy would be feasible and necessary, the following description focuses primarily on managing disease, traumatic injury, and associated inflammation of the human eye.

Histidine within the meaning of the invention encompasses each of the enantiomers D-histidine and L-histidine, racemic or non-racemic mixtures of histidine, or pharmaceutically acceptable salts thereof. The active agent of the present invention, histidine, in either of its enantiomeric forms, racemate form, free base, and salt forms is readily commerically available in USP grade and pyrogen-free from several sources. Salts of histidine include, for example, alkali and alkaline earth metals such as sodium and calcium, respectively, mineral acid salts such as HCl and sulfuric acid, or salts of organic acids, such as acetic acid. Amine addition salts may also be used in the practice of the invention, for example a phosphate amine addition salt. Where it is useful in the practice of the invention to employ a mixture of D- and L-histidine that is enriched in one enantiomer, such a mixture can be prepared by physically admixing the desired quantity of each of the enantiomers.

The novel methodologies, to be described in greater detail below, involve the administration of prophylactic or therapeutic amounts of histidine, either topically to the eye, orally, and/or intraveneously, to prevent ocular denegenerations or to treat (i.e., ameliorate or reduce) ocular inflammation and its associated cell-damage effects arising from numerous primary or secondary disease states, and surgical, chemical, or accidental physical traumas, respectively. Also the invention embodies the use of histidine to enhance post-surgical wound healing of the eye, to reduce the major drawbacks of certain refractive surgeries.

DETAILED DESCRIPTION OF THE INVENTION

Degenerative eye conditions within the purview of the preferred aspects of the invention include, for example, glaucoma, diabetic retinopathy, disease-based posterior vitreous detachment (PVD), age-based posterior vitreous detachment (PVD), corneal amyloidosis, age-related macular degeneration, retinal photic injury, retinal ischemia-induced eye injury, age-related macular degeneration, and free-radical-mediated diseases and/or injuries. Other degenerative ocular conditions well-known to those skilled in the art are also intended herein as the target of prophylaxis. See, for example, "The Cornea: Scientific Foundations and Clinical Practice", by Smolin, G. et al, Third Edition (1994), the entire contents of which are incorporated herein by reference.

In addition to the permanent damage caused by many degenerative eye diseases, inflammation is most often a sequela of the disease state. Hence, the discovery by the inventor that histidine can be administered to effectively treat ocular inflammation and its attendant cell damage associated with, for example, one or more diseases or degenerations including glaucoma, diabetic retinopathy, disease-based posterior vitreous detachment (PVD), age-based posterior vitreous detachment (PVD), corneal amyloidosis, age-related macular degeneration, retinal photic injury, retinal ischemia-induced eye injury, and free-radical-mediated diseases and/or injuries, Dellen, Terrein's Marginal Degeneration, and calcific band keratopathy.

Ocular inflammations arising from bacterial, viral, fungal, or parasitic infections occur with high frequency due to the sensitivity of eye tissue and its vulnerability to penetration. Inflammations from these origins are treatable within the context of the invention. More particularly, inflammation as a sequela of bacterial ocular infections arising from Pseudomonas, Staphylococcus sp., *Serratia marcescens,* Streptococcus sp., Haemophilus sp., *N. gonorrhoeae, N. meningitidis,* Moraxella, *Treponema pallidum, B. burgdorferi, Corynebacterium diphtheriae;* DNA viral ocular infections arising from one or more of Herpes simplex (HSV-1 and HSV-2), Varicella-zoster, Epstein-Barr, Adenovirus, Cytomegalovirus, and Papilloma; RNA viral ocular infections arising from one or more of Poliovirus, Enterovirus 70, Rhinovirus, Arbovirus, Influenza, Mumps, Measles, Rabies, and HIV, are treatable within the context of the present methods and compositions. Preferably, treatment of inflammation arising as a sequela of a Staphylococcus sp., and especially *S. aureus* and *S. epidermidis,* Pseudomonas, *Herpes simplex* (HSV-1 (oral) and HSV-2 (genital, the cause of ocular herpes in neonates)), and cytomegalovirus, with a therapeutically effective amount of histidine is a particularly preferred embodiment.

Further still, another preferred embodiment is the treatment of the following eye conditions or diseases, which may be either acute or chronic: allergic conjunctivitis, adenoviral keratoconjuctivitis, bacterial conjunctivitis, blepharitis, cytomegalovirus retinitis, edema, *H. simplex* epithelial keratitis, *H. zoster* keratitis, *H. zoster* iridocyclitis, interstitial keratitis, nummular keratitis, scleritis, trachoma, uveitis, and viral necrotizing keratitis. Corneal ulceration, corneal infiltration and corneal thinning, and inflammation associated therewith, are secondary sequelae of primary autoimmune or non-autoimmune diseases. Representative primary autoimmune diseases include ulcerative colitis, Mooren's ulcer, psoriasis, systemic lupus erythematosus, rheumatoid arthritis, Wegener's granulomatosis, polyarteritis nodosa, or myasthenia gravis. Representative non-autoimmune diseases include syphilis, gonorrhea, bacillary dysentery, leukemia, food allergy, and certain ocular dystrophies (e.g., macular dystrophy and Fuch's dystrophy.)

"*The Cornea: Scientific Foundations and Clinical Practice*", by Smolin, G. et al, Third Edition (1994), is a comprehensive treatise on corneal degenerations, diseases, inflammations, and ocular therapeutic/prophylactic agents, and the entire contents of which are incorporated herein by reference.

In an especially preferred embodiment, histidine is administered to a subject about to experience or having experienced ocular trauma, either from interventional/corrective ophthalmic surgical procedures, accidental physical blunt trauma, or chemical burn trauma.

In the case of interventional/corrective ophthalmic procedures, histidine is administered before, during and/or after the procedure to limit the inflammatory response that results from the incision of a cutting implement or laser. Another objective achieved by the administering of histidine in this setting is an observed improvement in post-surgical corneal wound healing. For example, corneal wound healing is an important determinant of the clinical outcome of laser-assisted photoablative surgical procedures such as excimer laser keratectomy, the main drawback of which is the development of "corneal haze". While many theories have been set forth for the cause(s) of corneal haze, improper collagen repair and/or collagen alignment, inflammation, and improper epithelial cell coverage of the cornea are believed to play a role in its formation. Histidine as a therapeutically active agent herein improves normal reepithelization of the cornea following photoablation, by promoting the regrowth flat (normal) keratocytes. Further, since PMNs of the inflammatory response are at the root of enzymatic degradation of collagen (i.e., they secrete collagenases), histidine's ability to limit the inflammatory process has a direct bearing on the control of collagen degradation and on collagen repair.

Accordingly, the present discovery includes treating the resultant inflammation and improving post-surgical wound healing in the following non-limiting representative procedures: radial keratotomy, cataract surgery, photoreactive keratectomy, laser in-situ keratomileusis, laser peripheral iridectomies, laser posterior capsulotomies, and laser-treated retinal/subretinal neovascularization. Any laser-assisted photoablative procedure causing a removal of corneal tissue and formation of haze is within the scope of the present prophylactic and therapeutic methods employing histidine as an active agent.

Inflammation associated with unintentional ocular burns arising from alkali, acid, and lacrimators (e.g., MACE, pepper spray) are also treatable by administering a therapeutically effective amount of histidine according to the invention. More particularly, alkali bums from, e.g., ammonia, lye (NaOH), potassium hydroxide, magnesium hydroxide, lime ($Ca(OH)_2$), and methyl ethyl ketone peroxide, result in an increase in the ocular pH, which leads to saponification of the fatty components of cell membranes, and ultimately cell disruption (or tissue damage.) Ammonia is the most damaging of the alkalis, since it is soluble in tears and the aqueous environment of the eye, forming ammonium hydroxide. Ammonium hydroxide is highly lipid soluble, rapidly penetrates the eye, and causes severe corneal injury with iris and lens damage. The fate of collagen in alkali burns is marked by a particularly destructive cascade of events. At high pH the alkali cations bind collagen (and glycoaminoglycans as well) of the stromal matrix, causing hydration or swelling and shortening of the collagen fibrils. Glaucoma is a common sequela of alkali burns, due to a rapid rise in intraocular pressure attributable to this shortening of collagen fibrils. The alkali also renders the collagen fibrils more susceptible to enzymatic degradation ("naked collagen".) A further exacerbation is that following chemical injury, corneal epithelium secrete collagenases, whereas normal (uninjured) corneal epithelial cells are not known to contain either latent or active collagenase. Further, if the alkali penetrates the ciliary body, the aqueous humor experiences a significant drop in aqueous glucose and ascorbate concentrations. Ascorbate is essential to the biosynthesis of both collagen and glycosaminoglycans.

Acid burns are more limited than alkali burns, due to the buffering capabilities of ocular tissue proteins. Representative examples of substances that cause acid burns include sulfuric acid, sulfurous acid, hydrochloric acid, hydrofluoric acid, chromic acid, nitric acid, and acetic acid. Acid burns cause tissue damage by coagulating and precipitating ocular proteins, and secondary glaucoma as the result of reacting with collagen (by fibril shortening.) In both alkali and acid burns, the course of therapy usually entails irrigating the eye, followed by administration of one or more of topical antibiotics, topical steroids, collagenase inhibitors, and anti-glaucoma agents, oral or topical ascorbate. It is intended that histidine be administered therapeutically following irrigation of the eye injured by an accidental chemical exposure. Histidine is preferably administered topically or orally, or by both routes. More preferably, histidine is administered as the active component in a therapeutic eye drop or ointment formulation. It is also an embodiment of the invention to coadminister a therapeutic dosage of histidine with a therapeutic dosage of one or more of the agents from the representative classes of burn remedies listed above; by way of non-limiting example topical antibiotics (e.g., 0.3% gentamicin drops or bacitracin ointment), topical steroids (e.g., 1% prednisolone, or 0.1% dexamethasone), collagenase inhibitors (e.g., 10–20% acetyl cysteine), anti-glaucoma agents (e.g, 10% phenylephrine) in combination with 2% atropine (a cycloplegic), and oral or topical ascorbate.

Ocular inflammations arising from accidental contact of the eye surface with cosmetics are also within the scope of the therapies disclosed herein. For example, the inflammation can be in response to a physical irritating aspect of the cosmetic formulation, such as agglomerated mascara particles or the particulate and powdery form of an eye shadow. Physical trauma to the eye surface from, for example, a mascara or liquid eyeliner brush may also contribute to the inflammation. Hence, it is within the purview of the invention to administer a therapeutic dose of histidine topically to the eye to reduce such inflammations subsequent to their ocurrence. Alternatively, another embodiment of the invention incorporates a therapeutically effective amount of histidine into, for example, a mascara formulation, a liquid eyeliner, or an eye creme. The physical compounding of efficacious amounts of histidine into certain cosmetic formulations can be accomplished using standard cosmetic formulary practices so long as doing so yields stable compositions useful for carrying out the present objectives.

It is also desirable to compound therapeutically effective amounts of histidine for topical application with eye cosmetic materials having cell regeneration activity. Preferably, histidine is compounded with one or more ($\alpha$- or $\beta$-) hydroxy acids and/or $\alpha$-ketoacids in, for example, an eye creme or mascara. Representative examples include, but are not limited to, free acids such as citric acid, glycolic acid, gluconic acid, lactic acid, malic acid, $\alpha$-hydroxybutyric acid, $\alpha$-hydroxyisobutyric acid, and ester, lactone, anhydride, amide or salt derivatives thereof.

Physical trauma can be a blunt injury, a penetrating injury, or a perforating foreign body which may be accompanied by intraocular inflammation, synechiae which leads to glaucoma, and secondary membrane formation. It is equally envisioned that histidine be administered during and after suturing to reduce the inflammation. Surgical adhesives (e.g., cyanoacrylates) and corneal mortars are an alternative to suturing, especially where the perforation or ulceration is severe. Accordingly, histidine is advantageously coadministered with the application of a surgical adhesiveor corneal mortar, and thereafter to treat the continuing inflammation.

In another preferred practice of the invention, a therapeutically effective amount of histidine is used in combination therapy with a broad range of presently available ocular therapeutics. Hence, histidine can be coadministered with at least one other therapeutically active agent in the same delivery vehicle/carrier either topically, orally, or intravenously. Alternatively, the combination therapy can be coadministered using separate routes and dosage forms, e.g., histidine eye drop and oral antibiotic, or oral histidine tablets and steroidal ointment. Within the scope of the invention, histidine is efficaciously combined with at least one of an antibiotic (e.g., beta-lactam type, fluoroquinolones, peptide antibiotics, broad-spectrum penicillins, fortified antibiotic mixtures), an antibacterial, a free-radical scavenging antioxidant, an antiviral, a corticosteroid, a non-steroidal antiinflammatory, a cycloplegic, a cholinergic, an aqueous or saline irrigating solution, a miotic, a collagenase inhibitor, a carbonic anhydrase inhibitor, a glycoprotein, a growth factor, silver nitrate, and an ocular tissue adhesive/corneal mortar (for acutely inflamed perforated corneas).

More particularly, by way of non-limiting example, histidine can be coadministered with a therapeutically effective amount of an antibiotic exemplified by ciprofloxacin, ofloxacin, norfloxacin, cefazolin, tobramycin, gentamycin, an aminoglycoside, a penicillin, a semisynthetic penicillin, amoxicillin, ampicillin, carbenicillin, ticarcillin, mezlocillin, a cephalosporin, vancomycin, chloramphenicol, erythromycin, clindamycin, rifampin, bacitracin, polymyxin, spectinomycin, a sulfonamide; and trimethoprim; a free-radical scavenging antioxidant exemplified by super oxide dismutase, a carotenoid (such as astaxanthin, canthazanthin, $\beta$-carotene, zeaxanthin, lutein and $\alpha$-tocopherol), ascorbic acid, glutathione, selenous acid or sodium selenate, and certain aminosteroids (e.g., as disclosed in U.S. Pat. No. 5,209,926); an antiviral exemplified by acyclovir, ganciclovir, idoxuridine, vidarabine, trifluridine, bromovinyldeoxyuridine, azidothymidine, amantadine, rimantadine; a corticosteroid exemplified by dexamethasone, prednisolone, prednisone, fluorometholone, betamethasone, hydrocortisone; an non-steroidal antiinflammatory agent exemplified by ketorolac, indomethacin, flurbiprofen, ketoprofen, loxoprofen, and diclofenac; a cycloplegic exemplified by atropine; a moitic exemplified by physostigmine, pilocarpine, and carbachol; an antiglaucoma agents exemplified by phenylephrine, acetazolamide, and timolol maleate; a collagenase inhibitor exmeplified by acetyl cysteine; a glycoprotein such as fibronectin and vitronectin, as well as analogs or fragments thereof, an ocular tissue adhesive as exemplified by isobutyl cyanoacrylate; a corneal mortar exemplified by fibronectin/growth factor (e.g., EGF) composition, optionally with a protein crosslinking agent (e.g., aldehydes and di-imidate esters); and various admixtures of the above materials.

The precise prophylactic or therapeutic dosage of histidine to be employed depends upon several factors, including the age and physical condition of the host, the nature and the severity of the ocular condition being treated, and the route of dosage administration. The assessment of these factors as well as the determination of the precise dosage is well within the skill of the treating ophthalmologist. In general, whether the compositions of the invention take the form of solution, suspension, emulsion (i.e., ointment), or solid preparation, the active histidine is present from about 0.01 to about 30 per cent by weight of the overall composition. For topical administration, prophylaxis and therapy can be expected when histidine is administered at a daily dosage of from about 0.001 mg to 300 mg, preferably from about 0.5 mg to 200 mg, and more preferably from about 1.0 to 100 mg daily depending on the nature of injury, extent of inflammation, or degeneration to be prevented. Since histidine is one of the body's naturally occurring amino acids, it does not suffer from the drawbacks (e.g., side effects and toxicity) that attend many therapeutic agents. Accordingly, histidine is well-tolerated at higher systemic levels.

Suitable carriers for ophthalmic solutions or suspensions include phosphate buffered saline, saline, water, lactated ringers or dextrose (5% in water). Such formulations may be conveniently prepared by admixing histidine with water to produce a solution or suspension which is filled into a sterile container and sealed against bacterial contamination. If suspensions are used, the particle size therein should be less than 10 $\mu$m to minimize eye irritation. Preferably, sterile materials are used under aseptic manufacturing conditions to avoid the need for terminal sterilization. The histidine solutions of the invention have a pH of between about 7 and about 10. To maintain the pH of these solutions, pH adjusting agents may be added. Examples of suitable pH adjusting agents include: a) mineral acids such as sulfuric acid, nitric acid and phosphoric acid; b) alkali salts such as sodium and potassium hydroxide; and c) organic acids such acetic and citric acids.

For ophthalmic histidine solutions any one or more the following formulation additives are suitable for inclusion. Wetting agents, demulcent polymers, and complexing agents may optionally be added to the solutions without comprising efficacy or stability. Buffers that may be employed in the present invention include boric acid and borate salts such as sodium borate; carbonate salts such as sodium carbonate and potassium carbonate. A buffer is generally present from about 0.05 weight percent to about 10 weight percent.

Tonicity agents that may be employed in the present invention include sodium chloride, potassium chloride, mannitol, propylene glycol, PEG 300, polyethylene glycol 400 (PEG 400), glycerine, polysorbate, sorbitol, dextran 40 and dextran 70.

The histidine compositions of the invention may also contain one or more preservatives for enhancing the shelf-life of the formulation. The preservatives may also function as absorption promoters by increasing the corneal and conjuctival penetration of histidine. Preservatives that may be employed herein include thimerosal, benzalkonium chloride, chlorhexidine digluconate, chlorobutanol, EDTA, methylparaban, propylparaban, sorbic acid, phenylmercuric acetate and phenylmercuric nitrate, with thimerosal being preferred. An effective amount of a preservative is generally from about 0.001 weight percent to about 0.75 weight percent. Absorption promoters, per se, e.g., taurocholic acid and saponin, are also contemplated for inclusion in the ocular histidine compositions to enhance ocular bioavailability.

Demulcent polymers are often incorporated into artificial tear formulations, and may optionally be added to any of the present histidine solutions. Because of their ability to hold large amounts of water, they are useful for coating and thus moisturizing the cornea of the eye. Cellulose derivative, Dextran 40, Dextran 70, gelatin and liquid polyols are among the demulcent polymers suitable for use with this invention.

Wetting agents such as polysorbates, poloxamer, tyloxapol and lecithin may optionally be added to optimally wet the surface of the eye.

The ophthalmic histidine solutions of the present invention are administered topically by applying them to the cul-de-sac of the eye from a dropper controlled bottle or dispenser. A typical dose regimen for an adult human may range from about 2 to about 8 drops per day (about 0.1 mg to about 10.0 mg of histidine). Dosages for adult humans may, however, be as high as about 100 mg histidine per day, in which case the drops are administered by "bunching", e.g., 5 doses administered over a 5 minute period, repeated 4 times daily. A topical solution in accordance with one embodiment of the invention comprises incorporating a therapeutic dose of histidine in an artificial tear formulation. Such artificial tear formulations are used for restoring the normal barrier function of damaged corneal epithelium following traumatic injury or surgery or for relief of dry eye syndrome. Typically, artificial tear compositions contain ionic components found in normal human tear film, as well as various combinations of one or more of tonicity agents (e.g., soluble salts, such as Na, Ca, K, and Mg chlorides, and dextrose and sorbitol), buffers (e.g., alkali metal phosphate buffers), viscosity/lubricating agents (e.g., alkyl and hydroxyalkyl celluloses, dextrans, polyacrylamides), non-ionic surfactants, sequestering agents (e.g., disodium edetate, citric acid, and sodium citrate), and preservatives (e.g., benzalkonium chloride, and thimerosal). The quantities and relative proportions of each of these components incorporated into an artificial tear composition are readily determinable by the skilled formulation chemist. The ionic species bicarbonate is used in artificial tear compositions, e.g., U.S. Pat. No. 5,403,598 and Ubels, J L, et al, *Arch. Ophthalmol.* 113(3) 371–8 (March, 1995). Artificial tear solutions containing both a therapeutic dose of histidine and bicarbonate are particularly useful in the practice of the invention.

Ophthalmic ointments have limited peak corneal drug level as compared to ophthalmic solutions, because in the former the drug must first dissolve in the precorneal tear film by penetrating the cornea. However, ophthalmic ointments have the benefit of providing prolonged drug contact time with the eye surface. Ophthalmic ointments according to the invention will include a base comprised of, for example, white petrolatum and mineral oil, often with anhydrous lanolin, polyethylene-mineral oil gel, and other substances recognized by the formulation chemist as being non-irritating to the eye, which permit diffusion of the drug into the ocular fluid, and which retain activity of the medicament for a reasonable period of time under storage conditions.

In an alternative embodiment, where the physical condition of the eye receiving the prophylaxis or treatment permits, the therapeutic dose of histidine can be administered in the form of a topical sustained-release ocular insert. Such inserts and suitable materials therefor (e.g., biocompatible, erodible polymers) are well-known to the skilled formulation chemist.

Further routes of administration suitable for the practice of the invention are intraocular injection (e.g., subconjunctival injection in treating uveitis) and intravenous administration. The therapeutic compositions herein most typically take the form of histidine solutions. Histidine may be used in free base or salt form (for example, salts of alkali and alkaline earth metals such as sodium and calcium, respectively, salts of mineral acids such as HCl and sulfuric acid, or salts of organic acids, such as acetic acid). Amine addition salts may also be used in the practice of the invention, for example a phosphate amine addition salt. Examples of typical carriers are sterilized water, saline, and phosphate buffered saline. Optional additives include isotonic agents, stabilizers, pH controlling agents, agents necessary for the proper infusion of solutions, and water soluble nutrients.

While it is most preferred to practice the methods of the invention by either topical administration or intraocular injection, prophylactic and therapeutic amounts of histidine can be administered orally. For these oral dosage forms, histidine is formulated with a pharmaceutically acceptable solid or liquid carrier. Solid form preparations include powders, tablets, pills, capsules, cachets, and dispersible granules. The concentration or effective amount of histidine to be administered per dosage is widely dependent on the actual condition being treated and the severity thereof. However, a total oral daily dosage ranges from about 50 mg to 30 g, and more preferably from about 250 mg to 25 g. A solid carrier can be one or more substances which may also function as a diluent, a flavoring agent, a solubilizer, a lubricant, a suspending agent, a binder, a preservative, a tablet disintegrating aid, or an encapsulating material. Suitable carriers include magnesium carbonate, magnesium stearate, talc, sugar, lactose, pectin, dextrin, starch gelatin, tragacanth, methylcellulose, sodium carboxymethylcellulose, microcrystalline cellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

Having now generally described the invention, the same will be better understood by reference to certain specific examples, which are included for purposes of illustration only and which are not intended to limit the invention, any embodiment thereof, or the reasonable scope of the appended claims.

CLINICAL PROTOCOL FOR MEASURING THE EFFECTS OF HISTIDINE ON POST-EXCIMER LASER KERATECTOMY-INDUCED LIGHT SCATTERING

Ten pigmented rabbits are used in the following experiments which are conducted in accordance with the Association of Research in Vision and Ophthalmology resolution on the use of animals in research. In the first treatment session the right eyes of each rabbit receive identical phototherapeutic keratectomies (PTK) using the VISX 20/20 argon fluoride excimer laser. The laser fluence is set at 160 mJ/cm$^2$, and the pulse repetition frequency is 5 Hz. Prior to surgery the animals are anesthetized with an intramuscular injection of a mixture of xylazine and ketamine hydrochloride (Rompun-Ketaset) in the proportions: 60% of 20 mg/ml Rompun to 40% of 100 mg/ml Ketaset by volume. In addition a topical anesthetic (0.5% tetracaine hydrochloride) and Atropine 1% are applied to each eye approximately 10 min before exposure. At the same time one drop of histidine (20% in sterile balanced saline solution, BSS) is applied to 5 eyes and one drop of drug vehicle (BSS) is applied to the other 5 eyes, which serve as controls.

In the identical PTK treatments, the epithelium is ablated to a depth of 40 μm over a central 6 mm diameter region of the cornea. A second drop of drug is applied to the experimental corneas and a drop of BSS is applied to the controls. After 1 minute, all corneas are flushed with BSS, dried with sterile cellulose sponges, and ablated to a stromal depth of 100 μm. Immediately after surgery, a third drop of drug solution is applied to the experimental corneas and a drop of BSS is applied to the controls. After 1 minute all corneas are again irrigated with BSS, after which erythromycin ointment is applied. Atropine and one drop of either drug or vehicle are applied daily for 4 days (until the epithelium has healed).

After two weeks the left eyes is given exactly the same treatment, except the experimental animals from the first treatment are now the controls and vice versa.

Treatment efficacy is determined using scatterometry. Baseline scatterometer readings are obtained on all eyes immediately prior to surgery and weekly thereafter for 5 weeks. After 5 weeks, scatterometer readings are taken bi-weekly until the rabbits are sacrificed (11 weeks for the right eyes and 9 weeks for the left eyes). For these measurements, the animals are anesthetized as described above and homatropine 1% is applied to dialate the pupil.

Scatterometer data are analyzed both in terms of relative scattering, in which each cornea serves as its own control, and in terms of scattering index, in which the scattering from each cornea is referenced to the average scattering of the corneas prior to treatment. The control and experimental data are analyzed using the students t-test.

EXAMPLE 1

Eye Drops

| | |
|---|---|
| L-histidine (.30 wt. % aqueous solution) | 15.0 ml |
| methyl cellulose solution (0.10 g methyl cellulose 0.09 g NaCl in 10 ml of sterile water) | 10.0 ml |
| physiological NaCl solution (pH 7.0–7.5) | 5 ml |

EXAMPLE 2

An eye drop formulation suitable for treating corneal ulcers is as follows:

| | | |
|---|---|---|
| L-histidine | .05 mg/ml | 5.0 ml |
| ciprofloxacin | 3 mg/ml | 5.0 ml |
| thimerosal | | 0.01 wt % |
| sterile water | | q.s. |

EXAMPLE 3

An artifical tear formulation has the following composition:

| Ingredient | Amount |
|---|---|
| histidine hydrochloride | 25 mg |
| sodium bicarbonate | 60 mg |
| sodium chloride (USP) | 33 mg |
| dextran 70 | 43 mg |
| hydroxyethyl cellulose | 45 mg |
| disodium edatate | 12 mg |
| potassium monophosphate | 30 mg |
| sodium phosphate, dibasic | 75 mg |
| distilled water | to 10 ml |

EXAMPLE 4

To promote healing after corneal alkali burns, a histidine ophthalmic ointment was prepared based on the following formulation:

| Ingredient | % Weight/Volume |
|---|---|
| Water | 3.2% |
| 80% White Petrolatum | 91% |
| 20% Mineral Oil | 2.9% |
| Anhydrous Liquid Lanolin | 2.9% |
| Histidine | 20.0% |

Histidine-ophthalmic ointment was compounded by dissolving histidine in distilled water and incorporating the solution into an ophthalmic ointment vehicle consisting of white petrolatum (94%), mineral oil (3%) and anhydrous liquid lanolin (3%). The final concentration of the histidine was 20.0%.

EXAMPLE 5

A combination therapy ointment for ocular burns has the following components:

|                     | % by weight |
|---------------------|-------------|
| D/L histidine       | 35%         |
| Prednisolone        | 5%          |
| Bacitracin          | 4%          |
| vegetable oil       | 10%         |
| acetyl lanolin      | 10%         |
| lanolin alcohol     | 12%         |
| sorbitol sesquioleate | 20%       |
| sterile water       | q.s.        |

EXAMPLE 6

A combination histidine antiviral therapy is provided for treatment of herpetic keratitis and associated inflammation and ocular tissue damage. An ointment containing 3.0% vidarabine ("Ara-A") and 20.0% L-histidine is applied to the cul-de-sac of the affected eye 5 times daily, for 14 days.

EXAMPLE 7

As a variation to the preceding example, a combination histidine-antiviral therapy is provided by topically administering 1.0% trifluridine ($F_3T$) drops every 1–2 hours by day, 9 doses daily for 14 days, and co-administering oral histidine tablets (250 mg, 4 times daily) for the same number of days. The histidine tablets are prepared according to the following general procedure: Histidine is mixed with lactose and starch. The mixture is wetted by a necessary amount of starch hydrogel, granulated and homogenized. Magnesium stearate is added with mixing. The mixture is then pressed into tablets.

EXAMPLE 8

A sterile 28.0 wt % histidine HCl solution is administered in the form of subconjunctival injection to treat uveitis. Alternatively, since subconjuntival injection can provoke anxiety in patients and is painful, the histidine HCl solution can be administered intravenously.

EXAMPLE 9

In subjects at risk for retinal ischemic injury, histidine is administered prophylactically as an intravenous infusion, prepared as follows. A specified number of moles of histidine (to obtain the desired dose and blood level concentration) are dissolved in sterilized water while stirring the solution to homogeneity. Acetic acid is added to the resulting aqueous solution of histidine to adjust the same to a pH of 7.0. The resulting aqueous solution is subjected to milipore filtration and charged under nitrogen gas into a vessel for an infusion solution. The product infusion solution is obtained by autoclaving according to accepted procedure.

EXAMPLE 10

A combination therapy ready-for-use i.v. solution contains 0.2% ciprofloxacin and 20% L-histidine in a 5% dextrose solution, is solubilized with lactic acid, and pH-adjusted with HCl.

EXAMPLE 11

The following combination therapy as an ophthalmic solution is intended to reduce inflammation and intraocular pressure following photoablation of the cornea to improve wound healing:

| D-histidine                  | 15 wt % |
|------------------------------|---------|
| physostigmine                | 0.5 wt %|
| hydroxypropyl methylcellulose| 0.5 wt %|
| purified water               | q.s.    |

EXAMPLE 12

In the treatment of ocular alkali burns, an eye drop containing as the active agents 10–20% acetylcysteine as a collagenase inhibitor and 22% histidine is administered to the affected eye 4 times daily for 10 days.

Alternatively, a combination therapy comprised of topical histidine eye drops (5.0 wt. % histidine, 2–4 drops, 4 times daily) oral acetazolamide (250 mg, 4 times daily) (for secondary glaucoma therapy) is suitable for alkali burns.

What I claim is:

1. A method for protecting a mammal from a degenerative eye condition comprising administering to a mammal suseptible to a degenerative eye condition a prophylactically effective amount of D-histidine, L-histidine, racemic or non-racemic mixtures of histidine, or pharmaceutically acceptable salts thereof.

2. The method according to claim 1 wherein said degenerative eye condition comprises glaucoma, diabetic retinopathy, disease-based posterior vitreous detachment (PVD), age-based posterior vitreous detachment (PVD), corneal amyloidosis, age-related macular degeneration, retinal photic injury, retinal ischemia-induced eye injury, age-related macular degeneration, or a free-radical-mediated ocular disease.

3. The method according to claim 1 wherein said prophylactically effective amount of D-histidine, L-histidine, racemic or non-racemic mixtures of histidine, or pharmaceutically acceptable salts thereof is administered intravenously, orally, topically to at least one eye, or a combination thereof.

4. The method according to claim 3 wherein said prophylactically effective amount of D-histidine, L-histidine, racemic or non-racemic mixtures of histidine, or pharmaceutically acceptable salts thereof is administered as an eye drop, an eye ointment, an intraocular injection or as an ocular insert.

5. A method for treating ocular inflammation associated with at least one of degenerative eye conditions, chronic eye conditions, a secondary sequela of primary disease, an infectious agent, an ophthalmic procedure, and unintentional eye trauma in a mammal comprising administering to said mammal a therapeutically effective amount of D-histidine, L-histidine, racemic or non-racemic mixtures of histidine, or pharmaceutically acceptable salts thereof.

6. The method according to claim 5 wherein said degenerative eye condition comprises glaucoma, diabetic retinopathy, disease-based posterior vitreous detachment (PVD), age-based posterior vitreous detachment (PVD), Dellen, Terrein's Marginal Degeneration, or calcific band keratopathy.

7. The method according to claim 5 wherein the secondary sequela of primary disease comprises at least one of corneal ulceration, corneal infiltration and corneal thinning caused by a primary autoimmune or non-autoimmune disease.

8. The method according to claim 7 wherein said primary autoimmune disease comprises ulcerative colitis, Mooren's ulcer, psoriasis, systemic lupus erythematosus, rheumatoid arthritis, Wegener's granulomatosis, polyarteritis nodosa, or myasthenia gravis.

9. The method according to claim 7 wherein said non-autoimmune disease comprises syphilis, gonorrhea, bacillary dysentery, leukemia, food allergy, ocular or dystrophies.

10. The method according to claim 5 wherein said infectious agent comprises a bacterium, a virus, a fungus, or a parasite.

11. The method according to claim 10 wherein the infectious agent is a bacterium comprising Pseudomonas, Staphylococcus sp., *Serratia marcescens,* Streptococcus sp., Haemophilus sp., *N. gonorrhoeae, N. meningitidis,* Moroxella, *B. burgdorferi, Corynebacterium diphtheriae,* or a combination thereof.

12. The method according to claim 11 wherein said Staphylococcus sp. is selected from the group consisting of *S. aureus* and *S. epidermidis.*

13. The method according to claim 7 wherein said infectious agent is a DNA virus selected from the group consisting of *Herpes simplex* (HSV-1 and HSV-2), Varicella-zoster, Epstein-Barr, Adenovirus, Cytomegalovirus, and Papilloma.

14. The method according to claim 7 wherein said infectious agent is an RNA virus selected from the group consisting of Poliovirus, Enterovirus 70, Rhinovirus, Arbovirus, Influenza, Mumps, Measles, Rabies, and HIV.

15. The method according to claim 5 wherein said eye inflammation is caused by an ophthalmic procedure involving a cutting implement or clinical or surgical use of a laser.

16. The method according to claim 15 wherein said eye inflammation is caused by photoreactive keratectomy, or laser in-situ keratomileusis, laser peripheral iridectomies, laser posterior capsulotomies, and laser-treated retinal/subretinal neovascularization.

17. The method according to claim 15 wherein said ophthalmic procedure is radial keratotomy or cataract surgery.

18. The method according to claim 5 wherein said eye inflammation is caused by an unintentional eye trauma.

19. The method according to claim 18 wherein said unintentional eye trauma comprises an acid chemical burn or an alkaline chemical burn.

20. The method according to claim 15 wherein said therapeutically effective amount of D-histidine, L-histidine, racemic or non-racemic mixtures of histidine, or pharmaceutically acceptable salts thereof is administered at a time comprising at least one of before, during, and after said ophthalmic procedure.

21. The method according to claim 15 wherein said therapeutically effective amount of D-histidine, L-histidine, racemic or non-racemic mixtures of histidine, or pharmaceutically acceptable salts thereof is administered intravenously, orally, topically, or a combination thereof.

22. The method according to claim 21 wherein said therapeutically effective amount of D-histidine, L-histidine, racemic or non-racemic mixtures of histidine, or pharmaceutically acceptable salts thereof is administered as an eye drop or an eye ointment.

23. The method according to claim 5 wherein said therapeutically effective amount of D-histidine, L-histidine, racemic or non-racemic mixtures of histidine, or pharmaceutically acceptable salts thereof is administered as an eye drop or an eye ointment.

24. A method for enhancing wound healing following a corneal excimer laser procedure comprising administering to a patient at a time comprising at least one of before, during, and after the corneal excimer laser procedure an amount of D-histidine, L-histidine, racemic or non-racemic mixtures of histidine, or pharmaceutically acceptable salts thereof effective to prevent a regrowth of non-planar keratocytes.

25. The method according to claim 24 wherein said therapeutically effective amount of D-histidine, L-histidine, racemic or non-racemic mixtures of histidine, or pharmaceutically acceptable salts thereof is administered intravenously, orally, topically to at least one eye, or a combination thereof.

26. The method according to claim 25 wherein said therapeutically effective amount of D-histidine, L-histidine, racemic or non-racemic mixtures of histidine, or pharmaceutically acceptable salts thereof is administered as an eye drop or an eye ointment.

27. The method according to claim 5 further comprising coadministering said therapeutically effective amount of histidine in combination with a therapeutically effective amount of at least one of an antibiotic, an antibacterial agent, an antioxidant, an antiviral agent, a corticosteroid, an hydroxyacid, a ketoacid, a non-steroidal antiinflammatory agent, a cycloplegic, a miotic, a collagenase inhibitor, an anti-glaucoma agent, a carbonic anhydrase inhibitor, a glycoprotein, and silver nitrate.

28. The method according to claim 27 wherein said therapeutically effective amount of histidine is coadministered with a therapeutically effective amount of at least one of ciprofloxacin, ofloxacin, norfloxacin, cefazolin, tobramycin, gentamycin, an aminoglycoside, a penicillin, a semisynthetic penicillin, amoxicillin, ampicillin, carbenicillin, ticarcillin, mezlocillin, a cephalosporin, vancomycin, chloramphenicol, erythromycin, clindamycin, rifampin, bacitracin, polymyxin, spectinomycin, a sulfonamide, trimethoprim, super oxide dismutase, astaxanthin, canthazanthin, β-carotene, zeaxanthin, lutein, α-tocopherol, ascorbic acid, glutathione, selenous acid, sodium selenate, acyclovir, ganciclovir, idoxuridine, vidarabine, trifluridine, bromovinyldeoxyuridine, azidothymidine, amantadine, rimantadine, dexamethasone, prednisolone, prednisone, fluorometholone, betamethasone, hydrocortisone, ketorolac, indomethacin, flurbiprofen, ketoprofen, loxoprofen, diclofenac, atropine, pilocarpine, carbachol, physostigmine, phenylephrine, acetazolamide, timolol maleate, fibronectin and vitronectin as well as analogs or fragments thereof, and acetyl cysteine.

29. The method according to claim 25 further comprising coadministering said therapeutically effective amount of histidine in combination with a therapeutically effective amount of at least one of an antibiotic, an antibacterial, an antioxidant, an antiviral, a corticosteroid, an hydroxyacid, a ketoacid, a non-steroidal antiinflammatory, a cycloplegic, a miotic, a collagenase inhibitor, an anti-glaucoma agent, a carbonic anhydrase inhibitor, a glycoprotein, and silver nitrate.

30. The method according to claim 29 wherein said therapeutically effective amount of histidine is coadministered with a therapeutically effective amount of at least one of ciprofloxacin, ofloxacin, norfloxacin, cefazolin, tobramycin, gentamycin, an aminoglycoside, a penicillin, a semisynthetic penicillin, amoxicillin, ampicillin, carbenicillin, ticarcillin, mezlocillin, a cephalosporin, vancomycin, chloramphenicol, erythromycin, clindamycin, rifampin, bacitracin, polymyxin, spectinomycin, a sulfonamide, trimethoprim, super oxide dismutase, astaxanthin, canthazanthin, β-carotene, zeaxanthin, lutein, α-tocopherol, ascorbic acid, glutathione, selenous acid, sodium selenate, acyclovir, ganciclovir, idoxuridine, vidarabine, trifluridine, bromovinyldeoxyuridine, azidothymidine, amantadine, rimantadine, dexamethasone, prednisolone, prednisone, fluorometholone, betamethasone, hydrocortisone, ketorolac, indomethacin, flurbiprofen, ketoprofen, loxoprofen, diclofenac, atropine, pilocarpine, carbachol, physostigmine, phenylephrine, acetazolamide, timolol maleate, fibronectin and vitronectin as well as analogs or fragments thereof, and acetyl cysteine.

31. The method according to claim 5 wherein said ocular inflammation is associated with a condition comprising allergic conjunctivitis, adenoviral keratoconjuctivitis, bacterial conjunctivitis, blepharitis, cytomegalovirus retinitis, edema, *H. simplex* epithelial keratitis, *H. zoster* keratitis, *H. zoster* iridocyclitis, interstitial keratitis, nummular keratitis, scleritis, trachoma, uveitis, or viral necrotizing keratitis.

32. The method according to claim 4 wherein said prophylactically effective amount of histidine is co-administered with at least one of an absorption promoter and an ophthalmic preservative.

33. The method according to claim 23 wherein said therapeutically effective amount of histidine is co-administered with at least one of an absorption promoter and an ophthalmic preservative.

34. The method according to claim 26 wherein said therapeutically effective amount of histidine is co-administered with at least one of an absorption promoter and an ophthalmic preservative.

35. A composition for administration to an eye to treat ocular inflammatory conditions, comprising a therapeutically effective amount of D-histidine, L-histidine, racemic or non-racemic mixtures of histidine, or pharmaceutically acceptable salts thereof, an ophthalomological carrier therefor, and optionally, formulation adjuvants.

36. The composition according to claim 35 wherein said ophthalmological carrier comprises a liquid, suspension, or emulsion.

37. The composition according to claim 35 wherein said formulation adjuvants comprise an absorption promoter, a tonicity agent, a pH-adjusting agent, a buffer, a viscosity/lubricating agent, a nonionic surfactant, a sequestering agent, a wetting agent, a preservative, or mixtures thereof.

38. The composition according to claim 35 further comprising a therapeutically effective amount of an additional therapeutically active material.

39. The composition according to claim 38 wherein said additional therapeutically active material comprises ciprofloxacin, ofloxacin, norfloxacin, cefazolin, tobramycin, gentamycin, an aminoglycoside, a penicillin, a semisynthetic penicillin, amoxicillin, ampicillin, carbenicillin, ticarcillin, mezlocillin, a cephalosporin, vancomycin, chloramphenicol, erythromycin, clindamycin, rifampin, bacitracin, polymyxin, spectinomycin, a sulfonamide, trimethoprim, super oxide dismutase, astaxanthin, canthazanthin, β-carotene, zeaxanthin, lutein, α-tocopherol, ascorbic acid, glutathione, selenous acid, sodium selenate, acyclovir, ganciclovir, idoxuridine, vidarabine, trifluridine, bromovinyldeoxyuridine, azidothymidine, amantadine, rimantadine, dexamethasone, prednisolone, prednisone, fluorometholone, betamethasone, hydrocortisone, an α-hydroxyacid, a β-hydroxyacid, an α-ketoacid, a β-ketoacid, ketorolac, indomethacin, flurbiprofen, loxoprofen, diclofenac, atropine, pilocarpine, carbachol, physostigmine, phenylephrine, acetazolamide, timolol maleate, fibronectin and vitronectin as well as analogs or fragments thereof, acetyl cysteine, or mixtures thereof.

40. The composition according to claim 35 wherein said therapeutically effective amount of histidine is formulated with bicarbonate in a liquid carrier to form an artificial tear solution.

41. The composition according to claim 36 wherein said ophthalmologic carrier is an emulsion to provide a histidine ointment.

42. An eye cosmetic composition comprising a mascara, a liquid eyeliner, or an eye creme and an antiinflammation effective amount of D-histidine, L-histidine, racemic or non-racemic mixtures of histidine, or pharmaceutically acceptable salts thereof.

43. A method of preventing or treating corneal haze formation in an eye of a patient to undergo or having undergone laser-assisted photoablative surgical procedure causing a removal of corneal tissue, comprising administering to said patient at a time comprising before, during, or after said photoablative procedure an amount of D-histidine, L-histidine, racemic or non-racemic mixtures of histidine, or pharmaceutically acceptable salts thereof, effective to prevent or treat corneal haze formation.

44. The method according to claim 43 wherein said amount of D-histidine, L-histidine, racemic or non-racemic mixtures of histidine, or pharmaceutically acceptable salts thereof, effective to prevent or treat corneal haze formation is administered topically or by intraocular injection to said eye of said patient.

45. The method according to claim 44 further comprising coadministering a therapeutic amount of an additional ocular therapeutic agent in combination with said amount of D-histidine, L-histidine, racemic or non-racemic mixtures of histidine, or pharmaceutically acceptable salts thereof.

* * * * *